United States Patent [19]

Monti

[11] Patent Number: 5,008,287

[45] Date of Patent: Apr. 16, 1991

[54] PHARMACEUTICAL COMPOSITIONS HAVING ANTINEOPLASTIC ACTIVITY

[75] Inventor: Sergio Monti, Lugano, Switzerland

[73] Assignee: Onco-Pharm Development AG, Vaduz/Lichtenstein, Fed. Rep. of Germany

[21] Appl. No.: 318,905

[22] Filed: Mar. 3, 1989

[30] Foreign Application Priority Data

Mar. 7, 1988 [CH] Switzerland ............................ 842/88

[51] Int. Cl.$^5$ ..................... A61K 31/28; A61K 31/095
[52] U.S. Cl. ...................................... 514/492; 514/706
[58] Field of Search ................................ 514/492, 706

[56] References Cited

U.S. PATENT DOCUMENTS 4,681,753  7/1987  Revili ................................. 514/492

FOREIGN PATENT DOCUMENTS 0095663  of 0000  European Pat. Off. .
2135885  of 0000  United Kingdom .

OTHER PUBLICATIONS

Schwarz et al., "Biological Potency of Organic Selenium Compounds IV, Straight-Chain Dialkylmono- and Diselenides", Bioinorganic Chemistry 3, 145–152 (1974).
2nd Int. Conf. Anticancer Res., vol. 8, (5 Part B), Oct. 11–15, 1988, pp. 1097–1098, Abstract 254; G. Scambia et al.: "Growth Inhibitory Effect of Diheptyl Diselenide (DHDSe) on Human Cancer in Vitro".
Journal Med. Chem., vol. 30, No. 4, 1987 pp. 597–602, Am. Chem. Soc.; S.-I. Kang et al.: "Linear Free Energy Relationships and Cytotoxicities of Para-Substitutes 2-Haloethyl Aryl Selenides and Bis(2-Chloroethyl)Selenides".
Journal of Pharmaceutical Sciences, vol. 69, No. 10, Oct. 1980, Am. Pharm. Ass.; Y. A. Beltagy et al.: "Antioxidants in Purification, Stabilization, and Formulation of the Antineoplastic Agent 6-Selenoguanosine".
Anticancer Research, vol. 9, 1989, pp. 1697–1700; G. Scambia et al.: "Growth Inhibitory Effect of Diheptyl Diselenide on Various Human Cancer Cell Lines".
Bioinorg. Chem., vol. 3, No. 2, 1974, pp. 145–152, Am. Elsevier Publ. Comn., Inc.; K. Schwarz et al.: "Biological Potency of Organic Selenium Compounds IV. Straight-Chain Dialkylmono-and Diselenides".

*Primary Examiner*—Jerome D. Goldberg
*Attorney, Agent, or Firm*—Ostrolenk, Faber, Gerb & Soffen

[57] ABSTRACT

Compositions containing as antineoplastic active principloe only dialkyl diselenides show a very promising activity not withstanding a remarkably lower toxicity in comparison with that of known combinations of the same dialkyldi selenides with other active principles.

6 Claims, No Drawings

PHARMACEUTICAL COMPOSITIONS HAVING ANTINEOPLASTIC ACTIVITY

The present invention refers to pharmaceutical compositions having antineoplastic activity against some kinds of tumors, containing as active principle a diselenide of formula I $$R—Se—Se—R' \quad (I)$$

wherein R and R' which can be the same or different represent a linear or branched $C_1$-$C_{20}$-alkyl or $C_2$-$C_{20}$-alkenyl group.

Swiss Patent 661865 claims antineoplastic compositions containing a combination of:
(a) diselenides of formula I (wherein, however, R and R' are alkyl or alkenyl groups having an odd number of carbon atoms) with
(b) an aliphatic carboxylic acid, aldehyde or ketone, having an odd number of carbon atoms.

The examples of said Swiss Patent refer to vials for intramuscular injection or capsules containing dipentyl-diselenide in combination with 3-heptanone.

During comparative tests on the anti-tumor activity of different agents, it has been found that the acute toxicity of the compositions claimed by Swiss Patent 661865 is quite higher as indicated in the Patent. Moreover, it has been surprisingly found that the acute toxicity of the diselenides of formula I alone is much lower than the acute toxicity of the corresponding combination of I with ketones (or aldehydes or acids), whereas the activity of I against some kinds of tumor remains unchanged.

This finding is above all surprising in view of the low toxicity of the ketones (or aldehydes or carboxylic acids) if administered alone; it is therefore logical to refer to a synergic toxicity of the compositions claimed by Swiss Patent 661865.

An object of the inventions is therefore provided by antineoplastic compositions containing as active principle exclusively diselenides of formula I.

Most of said diselenides are per se known since many years; moreover, K. Schwarz et al. (*Bioinorg. Chem.*, 1974, 3(2), 145-52) have disclosed the activity of diselenides of formula R'—Se—Se—R' (wherein R' is a saturated alkyl group containing 2-11 C-atoms) in preventing the necrotic degeneration of liver.

According to this invention diselenides of formula I can be used wherein R and R', which can be the same or different, represent linear or branched chain $C_1$-$C_{20}$-alkyl or $C_2$-$C_{20}$-alkenyl groups. More preferred alkyl groups are linear or branched $C_5$-$C_{12}$-alkyl groups and preferred alkenyl groups are linear or branched $C_5$-$C_{12}$-alkenyl groups.

Specific preferred compounds are:
di-n-pentyl-diselenide
di-n-hexyl-diselenide
di-n-heptyl-diselenide
di-n-octyl-diselenide
di-n-undecyl-diselenide
di-(3-methylbutyl)-diselenide
di-(4-methylpentyl)-diselenide
di-(5-methylhexyl)-diselenide
di-(7-methyl-octyl)-diselenide
n-pentyl-(3-methyl)butyl-diselenide
n-heptyl-(5-methyl)hexyl-diselenide
di-(4-hexen-1-yl)-diselenide
di-(5-hexen-1-yl)-diselenide
di-(6-hepten-1-yl)-diselenide
di-(10-undecen-1-yl)-diselenide.

The compounds of formula I, diluted with vegetal oils, particularly sesame oil and corn oil, in percentages from 0.5 to 5, preferably from 1 to 3% (w/v), show a remarkable antitumoral activity, in vivo in mice, against solid tumors. They are moreover active against leukemia, and have a high antimetastatic activity in cases in which the same compounds are inactive, or scarcely active, against the primary tumors.

The administration of diselenides in combination with ketones (or aldehydes or carboxylic acids) according to the claims and examples of Swiss Patent 661865, in the same conditions as for the compounds of formula I alone, induced so serious toxicity signs as to allow a further experimentation only with the proviso of reducing the administered doses to 1/10 of the original dosis.

The following examples, and the corresponding pharmacological and toxicological consideration, should not be understood to limit the invention; the results obtained with other compositions according to the invention are completely similar.

EXAMPLE 1

Twenty grams of diheptyl-diselenide are dissolved in 980 grams of corn oil. The clear solution is administered by oral route (in gelatine capsules containing 1-2 ml) or by parenteral route (in vials containing 0.5-1-2 ml).

EXAMPLE 2

The same composition of Example 1 is prepared, by substituting the corn oil with sesame oil.

REFERENCE EXAMPLE

According to Swiss Patent 661865 a solution is prepared from

| | |
|---|---|
| diheptyldiselenide | 2% (by weight) |
| 3-heptanone | 50% |
| sesame oil | 48% |

Toxicity

Two groups of 10 animals each of female C57B/ mice weighing in average 20 g were treated i.p. with 15 mg/kg of the composition of Example 1 and with 1.5 mg/kg of the reference example, respectively. The injection was repeated at the $4^{th}$, $7^{th}$ and $15^{th}$ day. At the $12^{th}$ day, in the group treated with the composition of Example 1, one animal died whereas the others survived without any toxicity symptoms. In the group treated according to the reference example, on the contrary, 4 animals were dead at the $12^{th}$ day and the others suffered of evident toxicity signs (decrease of food consumption, ataraxy), although treated with a 10-fold lower dose.

Anti-tumor activitY

Using the same treatment schedule as in the toxicity tests, the anti-tumor activity of the compositions of Example and of the reference example has been evaluated on mice bearing Lewis lung carcinoma. This kind of experimental tumor is known for its ability in inducing metastasis at pulmonary level.

From the results obtained, reported in the following Table, the antimetastatic activity of the composition of the invention is evident. As above reported, the toxicity turns out to be much lower for the composition of the invention in comparison with that of the reference composition. Both this toxicity difference and the antimetastatic activity found are highly significant.

TABLE

| Drug | Injection at days | | Dose i.p. | N. of animals | Dead | Mean Tumor weight |
|---|---|---|---|---|---|---|
| Ex. 1 | 1-4, | 7-11 | 20 mg/kg | 10 | 1 | 9 |
| Ref. Ex. | " | " | 2.0 mg/kg | 10 | 4 | 5 |
| Controls (oil) | " | " | 0.1 ml | 10 | — | 53 |
| Ex. 1 | " | " | 15 mg/kg | 10 | 1 | 8 |
| Ref. Ex. | " | " | 1.5 mg/kg | 10 | 2 | 2 |
| Controls | " | " | 0.1 ml | 10 | 0 | 49 |

The composition of the invention is also active against other experimental tumors, such as LI210 leukemia and solid sarcoma S180.

The compositions of this invention are therefore useful in the treatment of humans affected by tumoral pathologies of different origin.

The compositions will be formulated according to per se known methods. The preferred administration route will be the parenteral one (intravenous, intramuscular or subcutaneous) but other routes, such as the oral or topical ones, may be envisaged.

The posology and treatment schedule depend on several factors (kind of tumor, patient's conditions, optional combined treatment with other drugs) and can be determined by expert physicians according to usual methods. The pharmacological and toxicological results, anyhow, make foreseeable the possibility of administering, to a patient weighing 70 kg as an average, from 0.5 to 5 ml of the compositions of Examples 1 or 2 from 2 to 4 times a day, in therapy cycles ranging from 5 to 20 days.

I claim:

1. A method for treating a neoplasm sensitive to treatment with a selenium compound in a human consisting of administering to said humans in need thereof an effective amount of a diselenide of formula I $$R-Se-Se-R' \qquad (I)$$

wherein R and R' which can be the same or different represent a linear or branched chain $C_1$-$C_{20}$-alkyl or $C_2$-$C_{20}$-alkenyl group and a pharmaceutically acceptable vegetal oil carrier.

2. Method according to claim 1, wherein the diselenide is diheptyldiselenide.

3. Method according to claim 1 wherein the diselenide is dissolved in corn oil or sesame oil.

4. Method according to claim 1, wherein the percentage of the diselenide is from 0.5 to 5 (w/v).

5. Method according to claim 4, wherein the percentage of the diselenide is from 1 to 3% (w/v).

6. Method according to claim 1, wherein R and R' have 5 to 12 carbon atoms.

* * * * *